United States Patent [19]

Sugano et al.

[11] Patent Number: 4,563,306
[45] Date of Patent: Jan. 7, 1986

[54] PEPTIDES AND PROCESS FOR PREPARING THE SAME

[75] Inventors: Hiroshi Sugano, Nara; Ryuichi Ishida, Suita; Michio Yamamura, Tondabayashi, all of Japan

[73] Assignee: Tanabe Seiyaku Co., Ltd., Japan

[21] Appl. No.: 641,978

[22] Filed: Aug. 17, 1984

[30] Foreign Application Priority Data

Sep. 7, 1983 [GB] United Kingdom ................ 8323909

[51] Int. Cl.$^4$ ..................... C07C 103/52; A61K 37/00
[52] U.S. Cl. ............................. 260/112.5 TR; 514/18; 514/19
[58] Field of Search ................ 260/112.5 TR; 514/18, 514/19

[56] References Cited

U.S. PATENT DOCUMENTS 4,100,152 7/1978 Fujino et al. ............. 260/112.5 TR

Primary Examiner—Delbert R. Phillips
Attorney, Agent, or Firm—Jordan B. Bierman

[57] ABSTRACT

A compound of the formula:

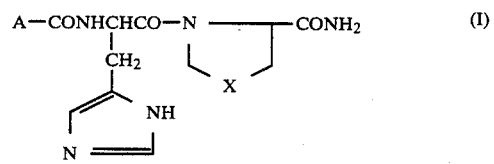

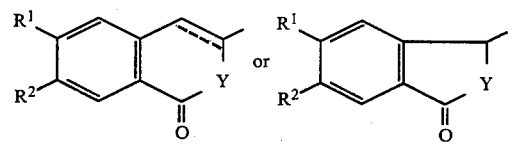

wherein
A is a group of the formula:

$R^1$ and $R^2$ are the same or different and each hydrogen atom, nitro, amino, a protected amino, hydroxy or lower alkoxy,
Y is oxygen atom or a group of the formula: $-NR^3-$,
$R^3$ is hydrogen atom or lower alkyl,
X is methylene or sulfur atom and
the dotted line is an optional double bond, or a pharmaceutically acceptable acid addition salt thereof is useful as a medicine for the treatment of consciousness disorders.

9 Claims, No Drawings

PEPTIDES AND PROCESS FOR PREPARING THE SAME

This invention relates to novel peptides of the formula:

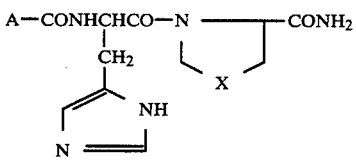 (I)

wherein
A is a group of the formula:

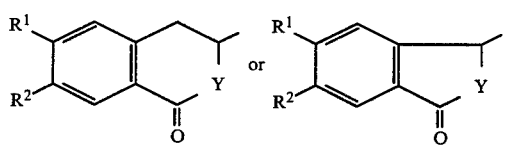

R¹ and R² are the same or different and are each hydrogen atom, nitro, amino, a protected amino, hydroxy or lower alkoxy,
Y is oxygen atom or a group of the formula: —NR³—,
R³ is hydrogen atom or lower alkyl,
X is methylene or sulfur atom and
the dotted line is an optional double bond, or a pharmaceutically acceptable acid addition salt thereof, and a process for preparation of the same.

It is known that TRH (i.e., thyrotropin releasing hormone; L-pyroglutamyl-L-histidyl-L-prolinamide) is useful as a medicine for treating consciousness disorders due to a brain dysfunction. In addition to this, however, TRH possesses the TSH (thyroid stimulating hormone)-releasing activity, which is considered to be an undesirable action for its therapeutic effect on the consciousness disorders.

As a result of various investigations, we have now found that the compound (I) of the present invention shows much stronger activating effects upon central nervous system (e.g., antagonistic effect on pentobarbital anesthesia, increasing effect on spontaneous locomotor activity, antagonistic effect on reserpine-induced hypothermia, potentiating effect on action of methamphetamine and have greater safty for use in treatment of central nervous system disorders (e.g., consciousness disorders) because of relatively less side effects (e.g., TSH-releasing activity) as compared with TRH.

Representative examples of the compound of the present invention include those of the formula (I) in which A is a group of the formula:

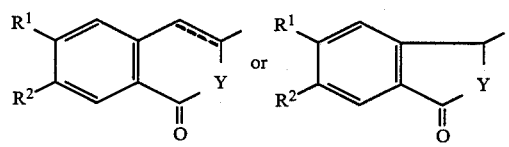

R¹ and R² are the same or different and are each hydrogen atom, nitro, amino, a protected amino (e.g., lower alkanoylamino such as acetylamino, lower alkoxycarbonylamino such as tert.-butyloxycarbonylamino, benzyloxycarbonylamino), hydroxy, or lower alkoxy of one to 4 carbon atoms (e.g., methoxy ethoxy, propoxy, butoxy), Y is oxygen atom or a group of the formula: —NR³—, R³ is hydrogen atom or lower alkyl of one to 4 carbon atoms (e.g., methyl, ethyl, propyl, butyl), X is methylene or sulfur atom and the dotted line is an optional double bond. Among them, a preferred subgenus is those of the formula (I) in which R¹ and R² are the same or different and each hydrogen atom, nitro, amino, lower alkoxycarbonylamino, hydroxy or methoxy and R³ is hydrogen atom or methyl. More preferred subgenus is those of the formula (I) in which A is a group of the formula:

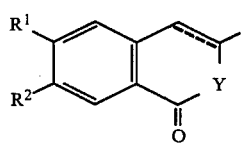

R¹ and R² are the same or different and each hydrogen atom, nitro, amino, tert.-butoxycarbonylamino, hydroxy or methoxy, Y is oxygen atom or a group of the formula: —NR³—, R³ is hydrogen atom or methyl and the dotted line is an optional double bond. Further preferred subgenus is those of the formula (I) in which A is a group of the formula:

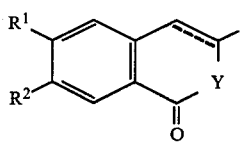

R¹ and R² are the same or different and each hydrogen atom, nitro or amino, Y is a group of the formula: —NR³—, R³ is hydrogen atom or methyl, X is methylene and the dotted line is an optional double bond. Further more preferred subgenus is those of the formula (I) in which A is a group of the formula:

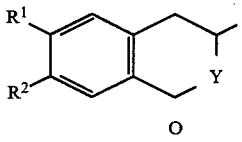

R¹ and R² are the same or different and each hydrogen atom or amino, Y is a group of the formula: —NR³—, R³ is hydrogen atom or methyl, X is methylene.

According to the present invention, the compound (I) can be prepared by condensing a compound of the formula:

A—COOH (II)

wherein A is the same as defined above, or a reactive derivative thereof with a compound of the formula:

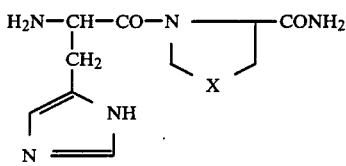

(III)

wherein X is the same as defined above, or a salt thereof.

Alternatively, the compound (I) can be prepared by condensing a compound of the formula:

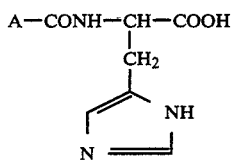

(IV)

wherein A is the same as defined above, or a reactive derivative thereof with a compound of the formula:

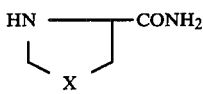

(V)

wherein X is the same as defined above, or a salt thereof.

The starting compounds (III) and (V) may be either in free form or in the form of a salt thereof. Examples of the salt of the compounds (III) and (V) include inorganic acid addition salts such as hydrochloride, hydrobromide, sulfate, nitrate, organic acid addition salts such as tosylate, methanesulfonate, trifluoroacetate and so forth. The compound (IV) may be obtained by condensing a compound of the formula (II) with histidine in conventional manners for peptide synthesis.

The condensation of the compound (II) or a reactive derivative thereof with the compound (III) or a salt thereof and the condensation of the compound (IV) or a reactive derivative thereof with the compound (V) or a salt thereof can be accomplished in conventional manners for the synthesis of peptides. For example, the condensation reaction of the reactive derivative of the compound (II) with the compound (III) or a salt thereof and the condensation reaction of the reactive derivative of the compound (IV) with the compound (V) or a salt thereof can be conducted either in the presence or absence of an acid acceptor in a solvent. Suitable examples of the reactive derivative of the compound (II) or (IV) include the corresponding acid halides (e.g., chloride, bromide), mixed anhydrides (e.g., a mixed anhydride of the compound (II) or (IV) with alkyl carbonate), active esters (e.g., pentachlorophenyl ester, p-nitrophenyl ester, 2,4-dinitrophenyl ester, succinimide ester, phthalimide ester, benzotriazole ester, 2-pyrrolidon-1-yl ester), acid azide and acid amides (e.g., imidazole amide, 4-substituted-imidazole amide, triazole amide). Dioxane, tetrahydrofuran, acetonitrile, methylene chloride, dimethylformamide, dimethylacetamide, ethyl acetate, pyridine, acetone and water are suitable as the solvent. Moreover, suitable examples of the acid acceptor include alkali metal hydroxides (e.g., potassium hydroxide, sodium hydroxide), alkali metal carbonates (e.g., sodium carbonate, potassium carbonate), alkali metal bicarbonates (e.g., sodium bicarbonate, potassium bicarbonate, trialkyl amines (e.g., trimethylamine, triethylamine), N,N-dialkylanilines (e.g., N,N-dimethylaniline, N,N-diethylaniline), pyridine and N-alkyl-morpholines (e.g., N-methylmorpholine). It is preferred to carry out the reaction at a temperature of −50° to 50° C., especially at −10° to 10° C.

On the other hand, the condensation reaction of the compound (II) in its free form with the compound (III) or a salt thereof and the condensation reaction of the compound (IV) in its free form with the compound (V) or a salt thereof can be conducted in the presence of a dehydrating agent in a solvent. Suitable examples of the dehydrating agent include dicyclohexylcarbodiimide, N-cyclohexyl-N'-morpholinocarbodiimide, N-ethyl-N'-(3-dimethylaminopropyl)carbodiimide, phosphorus oxychloride, phosphorus trichloride, thionyl chloride, oxalyl chloride, triphenylphosphine and the like. Vilsmeier reagent prepared from dimethylformamide and phosphorus oxychloride, from dimethylformamide and oxalyl chloride, from dimethylformamide and phosgen or from dimethylformamide and thionyl chloride may also be used as said dehydrating agent. It is preferred to carry out the reaction at a temperature of −50° to 50° C., especially at −20° to 20° C. Dioxane, tetrahydrofuran, acetonitrile, chloroform, methylene chloride, dimethylformamide, N,N-dimethylacetamide, ethyl acetate, pyridine, acetone and water are suitable as the solvent.

Further, the compound of the formula (I) in which at least one of $R^1$ and $R^2$ is amino can be prepared by removing a protecting group from a compound of the formula (I) in which at least one of $R^1$ and $R^2$ is a protected-amino. Said removal of the protecting group can be carried out in conventional manners. For example, if said protecting group is a lower alkoxycarbonyl group such as tert.-butyloxycabonyl, it is removed by treating the protected compound with a mineral acid (e.g., hydrochloric acid, hydrobromic acid, sulfuric acid) or an organic acid (e.g., trifluoroacetic acid). Besides, if said protecting group is benzyloxycarbonyl, it is removed by catalitically reducing the protected compound in the presence of a catalyst (e.g., Pd/C, Pt). Further, if said protecting group is a lower alkanoyl group such as acetyl, it is also removed by treating it with a mineral acid (e.g., hydrochloric acid, hydrobromic acid, sulfuric acid). Any other groups which have been usually used to protect amino group in peptide synthesis may be used to protect said amino group, and these groups may be readily removed therefrom by per se known methods.

In the above-mentioned reactions, the compounds (II) (in which A is a group of the formula:

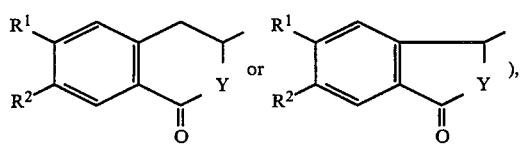

(III), (IV) and (V) may be used in the form of either optically active isomer or a mixture thereof. Since the above-mentioned reactions proceed without racemization, the compound (I) is readily obtained in the form of optically active isomer by the use of the corresponding optically active isomer of the compound (II), (III), (IV) or (V).

Among the starting compounds, the compound (II) in which $R^1$ and $R^2$ are each nitro, amino or a protected amino, is a novel compound and may be prepared, for example, by reacting a compound of the formula:

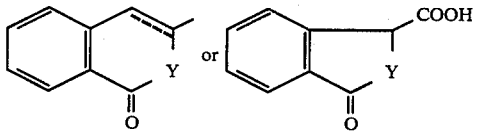

wherein Y and the dotted line are the same as defined above, with conc. sulfuric acid and nitric acid at $-50°$ C. to give the compound (II) in which either one or both of $R^1$ and $R^2$ are nitro, if required, reducing it in the presence of a catalyst (e.g., Pt, Pd, Ni) in a solvent (e.g., acetic acid, methanol) to give the compound (II) in which either one or both of $R^1$ and $R^2$ are amino, and if required, further introducing a protecting group or groups into the product thus obtained.

On the other hand, the starting compound (II) in which $R^1$ and $R^2$ are each hydroxy or lower alkoxy is also a novel compound and may be prepared by subjecting the compound (II) (in which either one or both of $R^1$ and $R^2$ are amino) to diazotization to give the compound (II) (in which either one or both of $R^1$ and $R^2$ are hydroxy), and if required, reacting it with di(lower alkyl) sulfate in a solvent (e.g., water, acetone, dimethylsulfoxide, dimethylformamide) in the presence of an acid acceptor (e.g., potassim hydroxide, sodium hydroxide, potassium carbonate) at $-10°$ to $20°$ C. Alternatively, the compound (II) in which A is a group of the formula:

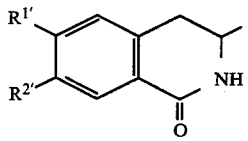

$R^{1'}$ and $R^{2'}$ are each hydroxy or lower alkoxy, may be prepared in conventional manners by the following reaction scheme:

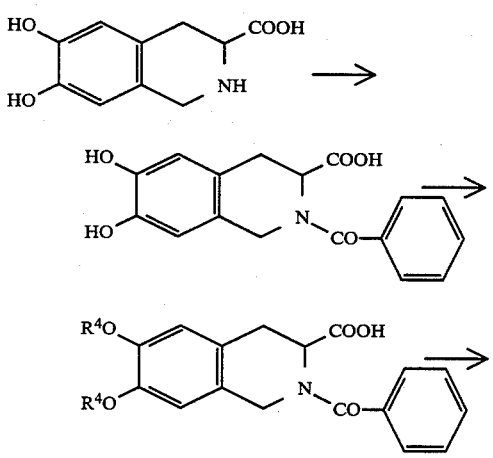

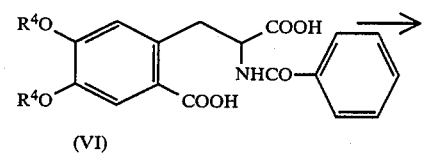

(VI)

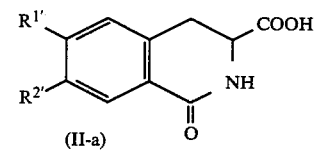

(II-a)

wherein $R^4$ is lower alkyl and $R^{1'}$ and $R^{2'}$ are the same as defined above.

The above-mentioned intramolecular cyclization may be carried out by the use of either hydrochrolic acid or hydrobromic acid. However, the compound (II-a) in which $R^{1'}$ and $R^{2'}$ are lower alkoxy may be obtained by treating the compound (VI) with 6N-HCl in acetic acid, and the compound (II-a) in which at least one of $R^{1'}$ and $R^{2'}$ is hydroxy can be obtained by treating the compound (VI) with 47% HBr in acetic acid. The compound (II) in which Y is a group of the formula: $-NR^3-$ and $R^3$ is lower alkyl may be prepared by reacting the compound (II) (Y=$-NR^3-$, and $R^3$=hydrogen atom) with lower alkyl halide (e.g., methyl iodide, ethyl iodide) in a solvent (e.g., dimethylformamide, tetrahydrofuran, acetone) in the presence of silver oxide to give a lower alkyl ester of the corresponding N-lower alkyl compound, and then hydrolyzing said compound with an alkali agent (e.g., sodium hydroxide, lithium hydroxide).

Further, the compound (III) in which X is sulfur atom may be prepared, for example, by condensing $N^{im}$-tosyl-$N^\alpha$-o-nitrophenylsulfenylhistidine [cf. Bull. Chem. Soc. Japan, 42, 1466 (1969)] with thiazolidine-4-carboxamide, followed by removing each protecting groups of the amino and imino groups.

The compound (I) may exist in the form of eight or four optical isomers due to the three or two asymmetric carbon atoms involved therein. All of those optical isomers or a mixture thereof are included within the scope of the invention. Among those isomers, however, when X in the formula (I) is methylene, preffered isomers useful for medicinal use are compounds of the formula (I) wherein the configuration at the sites of each asymmetric carbon is S-configuration, and when X is sulfur atom, preffered isomers are compounds of the formula (I) wherein the thizolidine moiety is R- and the other asymmetric carbons are S-configuration.

The compound (I) can be used for pharmaceutical use either as the free base or as an acid addition salt thereof. Pharmaceutically acceptable acid addition salts of the compound (I) are, for example, inorganic acid addition salts such as hydrochloride, hydrobromide, sulfate or nitrate; and organic acid addition salts such as acetate, maleate, tartrate, succinate, citrate, methanesulfonate, malate, oxalate or benzenesulfonate. These salts may be prepared, for example, by neutralizing the compound (I) with an acid. The compound (I) or a pharmaceutically acceptable acid addition salt thereof can be administered either orally or parenterally. Further, the compound (I) or its salt may be used in the form of a pharmaceutical preparation containing the same compound in conjunction or admixture with a pharmaceutical excipient suitable for oral or parenteral administration. Suitable excipients are, for example, starch, lactose, glucose, potassium phosphate, corn starch, arabic gum, stearic acid or other known medicinal excipients. The pharmaceutical preparation may be in solid form such as, for example, tablets, powders, capsules or granules; or in liquid form such as, for example, solutions or suspensions. Further, when administered parenterally, the pharmaceutical preparation may be used in the form of injections.

As mentioned hereinbefore, the compound (I) of the present invention has much stronger activating effects upon central nervous system (e.g., antagonistic effect on pentobarbital anesthesia, increasing effect on spontaneous locomotor activity, antagonistic effect on reserpine-induced hypothermia and potentiating effect on action of methamphetamine) with relatively less side effects (e.g., TSH-releasing activity) as compared with TRH. Therefore, the compound (I) of the present invention is much more useful as palinesthesias, spontaneous movement stimulants or dopamine potentiators than TRH. The compound (I) is also useful for the treatment of central nervous system disorders such as, for example, consciousness disorders, short attention span, speech disorders, hypobulia, Lennox syndrome, senile dementia, hypnotic intoxication, autism, hyperkinesia, schizophrenia, depression and parkinsonism in a warm-blooded animal including human being.

Therapeutic dose of the compound (I) or its salt depends on route of administration; the age, weight and condition of patients; and the particular disease to be treated. In general, however, it may be used at a dose of 0.0005 to 5 mg/kg/day, especially at a dose of 0.01 to 1 mg/kg/day in the case of oral administration; or at a dose of 0.001 to 0.1 mg/kg/day in the case of parenteral administration (e.g. intravenously, intramuscularly, subcutaneously).

Practical and presently preferred embodiments of the present invention are illustratively shown in the following lines.

Throughout the specification and claims, the term "lower alkoxy", "lower alkyl" and "lower alkanoyl" should be interpreted as referring to alkoxy of one to 4 carbon atoms, alkyl of one to 4 carbon atoms and alkanoyl of one to 4 carbon atoms, respectively.

EXPERIMENTS

The pharmacological activities of each test compound were tested by the following methods.

Methods (1) TSH-releasing activity:

A test compound dissolved in a 0.1% BSA (bovine serum albumin)-containing physiological saline was intravenously administered to a group of five male JCL: SD rats. Fifteen minutes after the administration, blood was taken from the abdominal aorta under anesthesia. Serum TSH levels were determined by the double-antibody radioimmunoassay method (Midgley et al., Endocrinology., 79, 10 (1966)). The BSA-containing physiological saline was used for control instead of the test compound solution.

(2) Antagonistic effect on pentobarbital anesthesia:

Pentobarbital sodium was intraperitoneally administered to a group of ten male STD/ddy mice at a dose of 55 mg/kg. Ten minutes after the administration of pentobarbital sodium, a test compound dissolved in physiological saline was intravenously administered to the mice which had lost the righting reflex. The duration of anesthesia was measured as the time from the end of administration of the test compound until the righting reflex regained. Physiological saline was used for control instead of the test compound solution (Prange et al., Life Science, 14, 447–455, (1974)).

(3) Increasing effect on spontaneous locomotor activity:

A group of five male STD/ddY mice were individually placed in Ambulometer (i.e., an apparatus for measuring spontaneous locomotor activity; manufactured by OHARA IKA Co.) for 30 minutes to acclimatize to the apparatus. Thereafter, a test compound dissolved in physiological saline was intraperitoneally administered to the mice and, immediately after administration of the test compound, the spontaneous locomotor activity was measured for 60 minutes. Physiological saline was used for control instead of the test compound solution.

(4) Antagonistic effect on reserpine-induced hypothermia:

A test compound dissolved in physiological saline was intraperitoneally administered to a group of five male STD/ddy mice, and the rectal temperature was measured 30, 60, 120 and 180 minutes after the administration of the test compound. The increase in temperature in the treated group was compared to that in the control group which received physiological saline instead of the test compound solution.

(5) Potentiating effect on methamphetamine-induced hyperlocomotion:

A group of ten male STD/ddY mice were individually placed in Ambulometer for 30 minutes to acclimatize to the apparatus. Thereafter, methamphetamine in a dose of 0.2 mg/kg and the test compounds in a dose producing no effect on the spontaneous motor activity per se were intraperitoneally injected simultaneously, and then the spontaneous locomotor activity was measured by the apparatus for 60 minutes.

Results

The results are shown in the following Table 1.

TABLE 1

| (Pharmacological activities of test compounds) | | |
|---|---|---|
| | Potency ratio relative to TRH* | |
| | TRH | $N^\alpha$—[(3S)-1-Oxo-1,2,3,4-tetrahydroisoquinoline-3-carbonyl]-L-hystidyl-L-prolinamide |
| TSH-releasing activity | 1 | 1 |
| Antagonistic effect on pentobarbital anesthesia | 1 | 10 |
| Increasing effect on spontaneous locomotor activity | 1 | 10 |
| Antagonistic effect on reserpine-induced hypothermia | 1 | 10 |
| Potentiating effect on action of methamphetamine | 1 | 10 |

Note:
*Potency ratio relative to TRH was calculated from the dose-response curves of TRH and $N^\alpha$—[(3S)-1-Oxo-1,2,3,4-tetrahydroisoquinoline-3-carbonyl]-L-histidyl-L-prolinamide by parallel line assay method.

EXAMPLE 1

(3S)-1-Oxo-1,2,3,4-tetrahydroisoquinoline-3-carboxylic acid [J. Am. Chem. Soc., 84, 4487(1982)] (956 mg, 5 mmole) and N-hydroxysuccinimide (633 mg, 5.5 mmole) are dissolved in dimethylformamide (DMF) (7 ml), and thereto is added dicyclohexylcarbodiimide (DCC) (1.2 g, 6 mmole) at 0° C. The mixture is stirred for 1.5 hours. The resulting solutin is designated "Solution A".

Separately, to a solution (7 ml) of L-histidyl-L-prolinamide.2HBr (1.66 g, 5 mmole) in DMF is added triethylamine (1.4 ml, 10 mmole) at 0° C. The mixture is stirred at 0° C. for 15 minutes. The precipitated triethylamine.HBr is filtered off and washed with DMF (7 ml). The filtrate and washing liquid are combined, and the combined solution is added to Solution A obtained above. The mixture is stirred at 10° C. for 2 days. Insoluble materials are filtered off, and the filtrate is distilled under reduced pressure to remove DMF. To the residue is added water, and insoluble materials are filtered off. The filtrate is passed through a column (3×38 cm) packed with styrene-divinylbenzene copolymer resin (MIC GEL CHP-20P, manufactured by Mitsubishi Kasei). After washing the column with water (1 liter), the product is eluted with 30% methanol. The fractions containing the desired product are collected, distilled under reduced pressure to remove methanol, and lyophilized to give $N^\alpha$-[(3S)-1-oxo-1,2,3,4-tetrahydroisoquinoline-3-carbonyl]-L-histidyl-L-prolinamide (1.07 g, yield: 50%) as colorless powder. Addition of water gives crystals of the product (0.8 g).

m.p. 101°–103° C. (decomp.).

$[\alpha]_D^{20} +25.6°$ (c=1, $H_2O$).

Analysis for $C_{21}H_{24}N_4O_6 \cdot 5/4 H_2O$: Calcd: C,56.42; H,5.97; N,18.80. Found: C,56.33; H,5,67; N,18.73.

IR$\gamma_{max}^{Nujol}$ (cm$^{-1}$): 3270, 1690, 1680, 1660, 1640.

EXAMPLE 2

(a) (3S)-1-Oxo-1,2,3,4-tetrahydroisoquinoline-3-carboxylic acid (960 mg, 5 mmole) and N-hydroxysuccinimide (690 mg, 6 mmole) are dissolved in DMF (12.5 ml), and thereto is added DCC (1.3 g, 6 mmole) at −5° to 0° C. The mixture is stirred at room temperature overnight. The precipitated dicyclohexylurea (DCU) is filtered off, and the filtrate is concentrated under reduced pressure at a temperature below 40° C. The residue is dissolved in dioxane (5 ml), and the resulting solution is added to a mixture of L-histidine (1.55 g, 10 mmole), sodium carbonate (1.1 g, 10 mmole) and water (5 ml) at 0° to 5° C. The reaction mixture is stirred at the same temperature overnight. The reaction mixture is adjusted to pH 2 with 10% hydrochloric acid, and insoluble materials are filtered off. The filtrate is washed with chloroform and then adsorbed onto a column packed with a sulfonated polystyrene-divinylbenzene resin (Dowex 50, H+ form, 75 ml). The column is washed with water until the washings become neutral, and then the product is eluted with 10% aqueous ammonia. The fractions being positive to Pauly reagent are collected and distilled under reduced pressure to remove water to give a crystalline product (1.8 g). This product is dissolved in water, and the solution is passed through a column (2.6×23 cm) packed with CHP-20P resin. The column is washed with water, and then the product is eluted with 30% methanol. The fractions being positive to Pauly reagent are collected, distilled to remove methanol and then lyophilized to give $N^\alpha$-[(3S)-1-oxo-1,2,3,4-tetrahydroisoquinoline-3-carbonyl]-L-histidine (380 mg, yield: 23%).

m.p. 200°–202° C. (decomp.), $[\alpha]_D^{25} +86.1°$ (c=1, $H_2O$).

(b) The histidine derivative (570 mg, 1.725 mmole) prepared in paragraph (a), L-prolinamide (235 mg, 1.8 mmole) and 1-hydroxybenzotriazole (245 mg, 1.8 mmole) are dissolved in DMF (9 ml), and thereto is added DCC (370 mg, 1.8 mmole) at −10° C. The mixture is stirred at −10° to 0° C. for one hour and further stirred at room temperature overnight. The precipitated DCU is filtered off. The filtrate is distilled under reduced pressure to remove DMF, and the residue is dissolved in 20% aqueous citric acid solution, and the solution is washed with ethyl acetate. The auqeous layer is adjusted to pH 9 with sodium carbonate and passed through a column (3×38 cm) packed with CHP-20P resin. The column is washed with water (one liter) and the product is eluted with 30% methanol. The fractions being positive to Pauly reagent are collected, distilled to remove methanol and then lyophilized to give $N^\alpha$-[(3S)-1-oxo-1,2,3,4-tetrahydroisoquinoline-3-carbonyl]-L-histidyl-L-prolinamide (550 mg) as colorless powder. Water is added to the product to crystalize it. The physical and chemical properties of this product are identical to those of the product prepared in Example 1.

EXAMPLE 3

(a) $N^{im}$-Tosyl-$N^\alpha$-o-nitrophenylsulfenyl-L-histidine (3.1 g, 6.7 mmole) and (4R)-thiazolidine-4-carboxamide (1.06 g, 6.7 mmole) are dissolved in a mixture of tetrahydrofuran (30 ml) and DMF (5 ml), and thereto is added DCC (1.7 g) at −5° to 0° C. The mixture is stirred at room temperature overnight, and the precipitated DCU is filtered off. The filtrate is distilled under reduced pressure to remove the solvent. The residue is dissolved in ethyl acetate (200 ml), and the solution is washed in 1N sulfuric acid, a saturated sodium bicarbonate solution and an aqueous saline solution and then dried. The solution is distilled to remove the solvent, and the residue is crystallized from ethyl acetate-petroleum ether. The crystals thus obtained are recrystallized from methanol to give (4R)-3-($N^{im}$-tosyl-$N^\alpha$-o-nitrophenylsulfenyl-L-histidyl)thiazolidine-4-carboxamide (1.8 g, yield: 46.5%).

m.p. 180°–182° C., $[\alpha]_D^{25} -36.2°$ (c=1, DMF).

(b) The thiazolidine-4-carboxamide derivative (670 mg) prepared in paragraph (a) is dissolved in a mixture of DMF (2 ml) and methanol (20 ml), and the mixture is cooled to 0° C. and then saturated with ammonia gas. The mixture is allowed to stand at room temperature overnight under being sealed. The reaction mixture is distilled to remove the solvent. The residue is dissolved in 20% aqueous citric acid solution, and the solution is washed with ethyl acetate and made alkaline with sodium bicarbonate. The mixture is extracted with ethyl acetate-tetrahydrofuran (5:1). The extract is washed with water, dried and then distilled to remove the solvent to give (4R)-3-($N^\alpha$-o-nitrophenylsulfenyl-L-histidyl)thiazolidine-4-carboxamide (400 mg, yield: 76.8%).

m.p. 70°–72° C. (decomp.), $[\alpha]_D^{25} -95.0°$ (c=0.5, methanol).

(c) The thiazolidine-4-carboxamide derivative (400 mg, 0.89 mmole) prepared in paragraph (b) is dissolved in dioxane (3 ml), and thereto is added dropwise 25% HCl-methanol (60 mg, 4 mmole). The mixture is stirred for 5 minutes, and thereto is added ether (5 ml). The precipitated (4R)-3-(L-histidyl)thiazolidine-4-carboxamide dihydrochloride is separated by filtration and dried.

Separately, (3S)-1-oxo-1,2,3,4-tetrahyroisoquinoline-3-carboxylic acid (70 mg, 0.36 mmole) and N-hydroxysuccinimide (41 mg, 0.36 mmole) are dissolved in DMF (5 ml) and thereto is added DCC (74 mg, 0.36 mmole) under ice-cooling. The mixture is stirred for 1.5 hours. To the solution of the activated ester thus prepared are added the (4R)-3-(L-histidyl)-thiazolidine-4-carboxamide dihydrochloride (150 mg, 0.4 mmole) prepared above and triethylamine (0.21 ml, 0.8 mmole) under ice-cooling. The mixture is stirred at 8° C. for 24 hours. The precipitated DCU is filtered off, and the filtrate is concentrated under reduced pressure. The residue is dissolved in water, and the solution is adjusted to pH 8 with sodium bicarbonate and is passed through a column (2.3×26 cm) packed with CHP-20P resin. The column is washed with water (500 ml) and further with 30% methanol (one liter), and then the product is eluted with 50% methanol. The fractions being positive to Pauly reagent are collected, distilled to remove methanol, and then lyophilized to give (4R)-3-{$N^\alpha$-[(3S)-1-oxo-1,2,3,4-tetrahydroisoquinoline-3-carbonyl]-L-histidyl}-thiazolidine-4-carboxamide (70 mg, yield: 41.8%).

$[\alpha]_D^{25}$ −6.1° (c=1, $H_2O$), $R_f$=0.6 (silica gel G; n-$C_4H_9OH$: $CH_3COOC_2H_5$: $CH_3COOH$: $H_2O$=1:1:1:1).

Analysis for $C_{20}H_{22}N_6O_4S.5/4H_2O$: Calcd: C, 51.65; H, 5.31; N, 18.07; S, 6.89. Found: C, 51.63; H, 5.04; N, 17.18; S, 6.66.

EXAMPLE 4

$N^\alpha$-[(3S)-1-Oxo-1,2,3,4-tetrahydroisoquinoline-3-carbonyl]-L-histidine (380 mg, 1.15 mmole), (4R)-thiazolidine-4-carboxamide (190 mg, 1.2 mmole) and 1-hydroxybenzotriazole (180 mg, 1.3 mmole) are dissolved in DMF (5 ml), and thereto is added DCC (270 mg, 1.8 mmole) at −10° C. The mixture is stirred at −10° to 0° C. for one hour and further at room temperature overnight. The precipitated DCU is filtered off, and the filtrate is concentrated under reduced pressure. The residue is dissolved in 20% aqueous citric acid solution. The solution is washed with ethyl acetate and is adjusted to pH 8 with sodium carbonate. The aqueous solution is passed through a column (2.3×26 cm) packed with CHP-20P resin. The column is washed with water (one liter) and with 30% methanol (1.2 liter). The product is eluted with 50% methanol. The fractions being positive to Pauly reagent are collected and lyophilized to give (4R)-3-{$N^{6o}$-[(3S)-1-oxo-1,2,3,4-tetrahydroisoquinoline-3-carbonyl]-L-histidyl}-thiazolidine-4-carboxamide (280 mg, yield: 51.9%). The physical and chemical properties of this product are identical to those of the product prepared in Example 3.

EXAMPLE 5

(3S)-7-Nitro-1-oxo-1,2,3,4-tetrahydroisoquinoline-3-carboxylic acid (400 mg, 1.7 mmole) and N-hydroxysuccinimide (200 mg, 1.7 mmole) are dissolved in DMF (15 ml), and thereto is added DCC (400 mg, 1.9 mmole) at 9° C. The mixture is stirred for 1.5 hours to give a solution of an activated ester.

To the solution obtained above are added L-histidyl-L-prolinamide.2HBr (743 mg, 1.8 mmole) and triethyolamine (0.75 ml, 5.35 mmole) at −5° to 0° C., and the mixture is stirred for 2 days. The precipitated DCU is filtered off, and the filtrate is distilled to remove DMF under reduced pressure. The residue is dissolved in water, and the aqueous solution is passed through a column (3×33 cm) packed with CHP-20P resin. The column is washed with water (one liter) and 30% methanol (one liter). The product is eluted with 50% methanol. The fractions being positive to Pauly reagent are collected and distilled to remove methanol. To the residue is added 1% hydrochloric acid (5 ml), and the mixture is lyophilized to give $N^\alpha$-[(3S)-7-nitro-1-oxo-1,2,3,4-tetrahydroisoquinoline-3-carbonyl]-L-histidyl-L-prolinamide hydrochloride (600 mg, yield: 70%).

m.p. 135°–140° C., $[\alpha]_D^{20}$ +21.6° (c=1, $H_2O$).

Analysis for $C_{21}H_{23}N_7O_6.HCl.3H_2O$: Calcd: C, 45.04; H, 5.22; N, 17.51. Found: C, 45.75; H, 5.46; N, 17.13.

EXAMPLE 6

(3R)-1-Oxo-1,2,3,4-tetrahydrisoquinoline-3-carboxylic acid [J. Am. Chem. Soc., 84, 4487(1962)] (500 mg) is dissolved in DMF (8 ml), and N-hyroxysuccinimide (322 mg) and DCC (580 mg) are added thereto to 0° C. The mixture is stirred for 1.5 hours. L-Histidyl-L-prolinamide.2HBr (1.1 g) and triethylamine (1.1 ml) are added to the mixture, and the mixture is stirred for 2 days. Insoluble materials are filtered off, and the filtrate is distilled under reduced pressure to remove DMF. The residue is acidified with 10% HCl, washed with chloroform and then adjusted to pH 8 with sodium bicarbonate. The resulting solution is passed through a column (2×30 cm) packed with CHP-20P resin. The column is washed with water (one liter) and the product is eluted with 30% methanol. The fractions which are positive to Pauly reagent are collected, and the collected solution is distilled under reduced pressure to remove methanol. The residue is lyophilized, whereby $N^\alpha$-[(3R)-1-oxo-1,2,3,4-tetrahydroisoquinoline-3-carbonyl]-L-histidyl-L-prolinamide (480 mg) is obtained. Yield: 41.7%.

$[\alpha]_D^{25}$ −131.0° (c=1, $H_2O$).

Analysis for $C_{21}H_{24}N_6O_4.H_2O$: Calcd: C, 57.00; H, 5.92; N, 18.99. Found: C, 56.70; H, 5.72; N, 19.28.

EXAMPLE 7

A solution of (3R)-2-methyl-1-oxo-1,2,3,4-tetrahydroisoquinoline-3-carboxylic acid (350 mg), DCC (412 mg) and DMF (8 ml) is stirred at 9° C. for 1.5 hours, and L-histidyl-L-prolinamide.2HBr (702 mg) and triethylamine (0.49 ml) are added thereto. The mixture is stirred for 2 days. Insoluble materials are filtered off, and the filtrate is distilled under reduced pressure to remove DMF. The residue is dissolved in an aqueous sodium bicarbonate solution, and the solution is passed through a column (2.4×21 cm) packed with CHP-20P resin. The column is washed with water (one liter), and the product is eluted with 30% methanol. The fractions positive to Pauly reagent are collected, and the collection solution is distilled to remove methanol. The residue is lyophilized, whereby $N^\alpha$-[(3S)-1-oxo-2-methyl-1,2,3,4-tetrahydroisoquinoline-3-carbonyl]-L-histidyl-L-prolinamide (370 mg) is obtained. Yield: 47.6% m.p. 140°–145° C., $[\alpha]_D^{25}$ −50.2° (c=1, $H_2O$)

Analysis for $C_{22}H_{26}O_4N_6.H_2O$: Calcd: C, 57.88; H, 6.18; N, 18.41. Found: C.58.25; H, 5.92; N, 18.40.

EXAMPLE 8

A mixture of (3S)-1-oxo-7-tert.-butyloxycarbonylamino-1,2,3,4-tetrahydroisoquinoline-3-carboxylic acid (680 mg), N-hydroxysuccinimide (280 mg), DCC (500 mg) and DMF (7 ml) is stirred for 1.5 hours. L-Histidyl-L-prolinamide.2HBr (990 mg) and triethylamine (1 ml) are added to the mixture. The mixture is stirred for 2 days. Insoluble materials are filtered off, and the filtrate is distilled under reduced pressure to remove DMF. The residue is dissolved in 20% citric acid, and washed with chloroform. The washed solution is adjusted to pH 9, and the solution is passed through a column (2.6×20 cm) packed with CHP-20P resin. The column is washed with water (one liter) and 30% methanol (1.5 liter) successively, and then the product is eluted with 50% methanol. The fraction positive to Pauly reagent are collected, and the collected solution is lyophilized, whereby $N^\alpha$-[(3S)-1-oxo-7-tert.-butyloxycarbonylamino-1,2,3,4-tetrahydroisoquinoline-3-carbonyl]-L-histidyl-L-prolinamide (400 mg) is obtained. Yield: 33.3%.

$[\alpha]_D^{25}$ −12.8° (c=0.5, $H_2O$).

Analysis for $C_{26}H_{33}N_7O_6 \cdot 2H_2O$: Calcd: C,54.25; H,6.47; N,17.03. Found: C,54.32; H,6.14; N,17.49.

EXAMPLE 9

(3RS)-3,4-Dihydroisocoumarin-3-carbxylic acid [Acta. Chem. Scand., 14, 539(1960)] (1.23 g), pentachlorophenol (1.86 g) and DCC (1.45 g) are dissolved in DMF (10 ml), and the mixture is stirred at 0° C. for 1.5 hours. The resulting solution is designated "Solution A". On the other hand, L-histidyl-L-polinamide.2HBr (2.64 g) is dissolved in DMF (15 ml), and triethylamine (1.29 g) is added thereto at 0° C. The precipitated triethylamine HBr is filtered off. The filtrate is added to Solution A obtained above. The mixture is stirred at 0° C. for 4 hours and then at 10° C. for 2 days. The precipitates are filtered off, and the filtrate is distilled under reduced pressure to remove DMF. Water is added to the residue, and the aqueous solution is washed with chloroform. The aqueous solution is passed through a column (26×35 cm) packed with CHP-20P resin. The column is washed with water (one liter) and 30% methanol, successively. The product is eluted with 50% methanol. The fractions positive to Pauly reagent are collected, and the collected solution is condensed. The residue is purified with silica gel column chhromatrography (Solvent: chloroform:methanol=85:15). The eluate thus obtained is again passed through a column packed with CHP-20P resin, and the product is eluted in the same manner as mentioned above. The fractions positive to Pauly reagent are collected and then lyophilized, whereby $N^\alpha$-[(3RS)-3,4-dihydroisocoumarin-3-cabonyl]-L-histidyl-L-prolinamide (1.27 g) is obtained. Yield: 47%.

$[\alpha]_D^{25}$ −65.8° (C=1, $H_2O$).

IR $\nu_{max}^{nujol}$ (cm$^{-1}$): 1730, 1675, 1640.

Analysis for $C_{21}H_{23}N_5O_5 \cdot H_2O$; Calcd: C,56.87; H,5.68; N,15.80. Found: C,57.13; H,5.43; N,15.76.

EXAMPLE 10 TO 16

The following compounds are obtained from the corresponding starting compound (II) and L-histidyl-L-prolinamide in the same manner as described in Example 9.

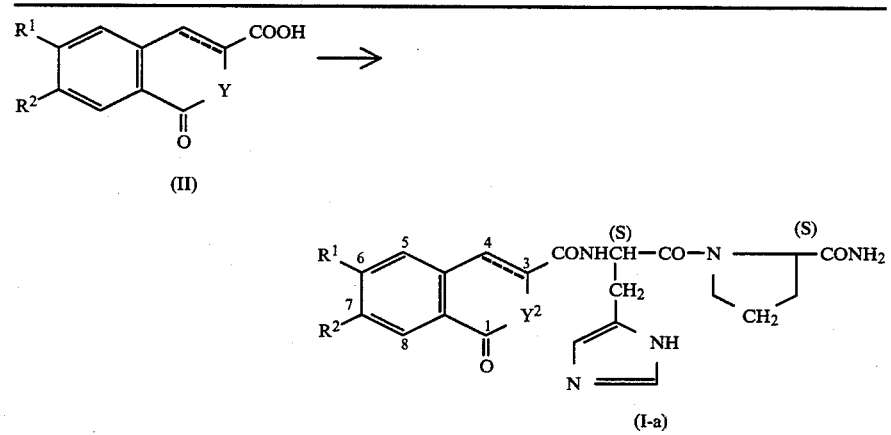

| Example Nos. | R$^1$ | R$^2$ | Y | C$_3$-C$_4$ bond | Configuration* | Yield etc. |
|---|---|---|---|---|---|---|
| 10 | H | H | O | single bond | 3S | Yield: 56%, $[\alpha]_D^{25}$ −60.7°(c = 1, $H_2O$), IR$\nu_{max}^{KBr}$ (cm$^{-1}$): 1725, 1675, 1640, Analysis for $C_{21}H_{23}N_5O_5$ Calcd: C, 59.28; H, 5.45; N, 16.47 Found: C, 59.38; H, 5.56; N, 16.39 |
| 11 | H | H | O | single bond | 3R | Yield: 52%, $[\alpha]_D^{25}$ −72.9° (c = 1, $H_2O$), IR$\nu_{max}^{KBr}$ (cm$^{-1}$): 1725, 1675, 1640 Analysis for $C_{21}H_{23}N_5O_5$ Calcd: C, 59.28; H, 5.45; N, 16.47 Found: C, 59.50; H, 5.30; N, 16.45 |
| 12$^a$ | H | H | NH | double bond | — | Yield: 63%, $[\alpha]_D^{27}$ −96.2° (c = 1, $H_2O$), IR$\nu_{max}^{KBr}$ (cm$^{-1}$): 1630 Analysis for $C_{21}H_{22}N_6O_4 \cdot HCl \cdot 2H_2O$ Calcd: C, 51.17; H, 5.52; N, 17.05 Found: C, 50.70; H, 5.04; N, 17.08 |
| 13$^b$ | H | H | O | double bond | — | Yield: 15%, $[\alpha]_D^{24}$ −81.2° (c = 1, $H_2O$) IR$\nu_{max}^{KBr}$ (cm$^{-1}$): 1730, 1665, 1630 Analysis for $C_{21}H_{21}N_5O_5 \cdot HCl \cdot 3/2H_2O$ Calcd: C, 51.80; H, 5.17; N, 14.38 Found: C, 51.34; H, 4.90; N, 14.12 |
| 14 | CH$_3$O | CH$_3$O | NH | single | 3S | Yield: 63%, $[\alpha]_D^{24}$ +10.2° (c = 1, $H_2O$) |

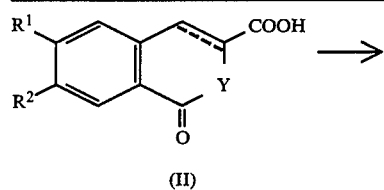

(II)

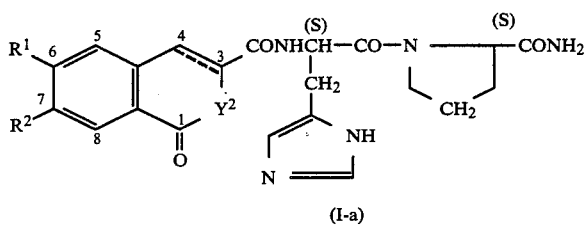

(I-a)

| Example Nos. | R¹ | R² | Y | C₃-C₄ bond | Configuration* | Yield etc. |
|---|---|---|---|---|---|---|
| | | | | bond | | IR$\nu_{max}^{KBr}$ (cm⁻¹): 1640, 1605 <br> Analysis for C₂₃H₂₈N₆O₆·2H₂O <br> Calcd: C, 53.06; H, 6.19; N, 16.14 <br> Found: C, 53.42; H, 5.63; N, 16.04 |
| 15 | HO | HO | NH | single bond | 3S | Yield: 37%, m.p. 199-204° C. <br> $[\alpha]_D^{21}$ −10.0° (c = 1, methanol), <br> IR$\nu_{max}^{nujol}$ (cm⁻¹): 1690, 1640, 1610 <br> Analysis for C₂₁H₂₄N₆O₆·3/2H₂O <br> Calcd: C, 52.17; H, 5.63; N, 17.39 <br> Found: C, 52.04; H, 5.40; N, 17.49 |
| 16 | CH₃O | HO | NH | single bond | 3S | Yield: 49%, $[\alpha]_D^{21}$ −7.2° (c = 1, H₂O), <br> IR$\nu_{max}^{nujol}$ (cm⁻¹): 1640 <br> Analysis for C₂₂H₂₆N₆O₆·H₂O <br> Calcd: C, 54.09; H, 5.78; N, 17.20 <br> Found: C, 54.00; H, 5.56; N, 17.10 |

[a]The starting compound: J. Pharmaceutical Society of Japan 81, 940(1960)
[b]The starting compound: J. Biol. Chem., 243, 2607(1968)
*Configuration at 3rd-position of 1,2,3,4-tetrahydroisoquinoline or 3,4-dihydroisocoumarin structure.

EXAMPLES 17 TO 18

The following compounds are obtained from the corresponding starting compound (II) and L-histidyl-L-prolinamide in the same manner as described in Example 9.

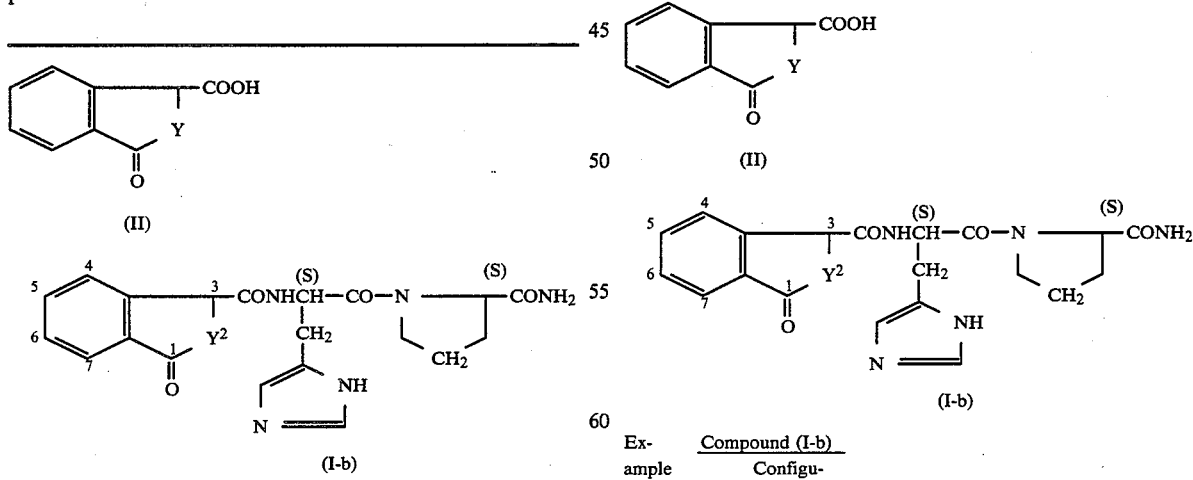

(I-b)

| Example Nos. | Compound (I-b) Y | Configuration* | Yield etc. |
|---|---|---|---|
| 17[a] | NH | 3RS | Yield: 33%, $[\alpha]_D^{27}$ −68.6° (c = 1, H₂O) <br> Analysis for C₂₀H₂₂N₆O₄·5/2H₂O <br> Calcd: C, 52.74; H, 5.98; N, 18.46 <br> Found: C, 52.64; H, 5.21; N, 18.36 |
| 18[b] | O | 3RS | Yield: 15%, m.p. 220-223° C. <br> $[\alpha]_D^{24}$ −34.4° (c = 1, methanol) <br> (R$\nu_{max}^{nujol}$ (cm⁻¹): 1770, 1670, 1630 <br> Analysis for C₂₀H₂₁N₅O₅ <br> Calcd: C, 58.38; H, 5.15; N, 17.03 |

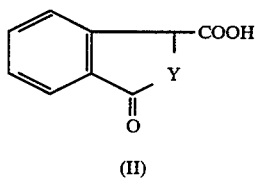

(II)

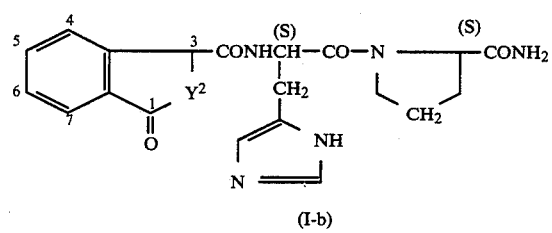

(I-b)

| Ex-ample Nos. | Compound (I-b) Y | Configu-ration* | Yield etc. |
|---|---|---|---|
| | | | Found: C, 58.27; H, 5.08; N, 16.95 |

<sup>a</sup>: The starting compound: J. Prakt. Chem., 146, 307(1936)
<sup>b</sup>:The starting compound: Ind. J. Chem., 19B, 473(1980)
*: Configuration at 3rd-position of isoindoline or 1,3-dihydroisobenzofuran structure.

EXAMPLE 19

N$^\alpha$-[(3S)-1-Oxo-7-tert-butyloxycarbonylamino-1,2,3,4-tetrahydroisoquinoline-3-carbonyl]-L-histidyl-L-prolinamide (710 mg) obtained in Example 8 is dissolved in a mixture of anisol (0.5 ml) and trifluoroacetic acid (5 ml), and the mixture is stirred for 30 minutes. The mixture is distilled to remove trifluoroacetic acid. Water (100 ml) and ether (50 ml) are added to the residue, and the mixture is stirred. The aqueous layer is collected, washed with ether and then adjusted to pH 9. The aqueous solution is passed through a column (2.8×33 cm) packed with CHP-20P resin. The column is washed with water and the product is eluted with 30% methanol. The fraction positive to Pauly reagent is collected, and the collected solution is distilled to remove methanol. The residue is lyophilied, whereby N$^\alpha$-[(3S)-1-oxo-7-amino-1,2,3,4-tetrahydroisoquinoline-3-carbonyl]-L-histidyl-L-prolinamie (700 mg) are obtained. Yield: 100%

$[\alpha]_D^{25}$ −24.5° (c=1, water).

Analysis for $C_{21}H_{25}N_7O_4H_2O$: Calcd: C,55.13; H,5.94; N,21.43. Found: C,54.99; H,5.91; N,21.55.

PREPARATION OF THE STARTING COMPOUNDS

Preparation 1

(3S)-1-Oxo-1,2,3,4-tetrahydrisoquinoline-3-carboxylic acid (1 g, 5.2 mmole) is dissolved in conc. sulfuric acid (4.5 ml) at a temperature below 10° C., and thereto is added gradually nitric acid (specifically gravity: 1,38, 0.86 ml) at −5° C. over a period of about one hour. The mixture is stirred at 20° C. for 30 minutes. The reaction mixture is poured onto ice (5 g). The precipitated crystals are separated by filtration, washed with water and dried to give (3S)-7-nitro-1-oxo-1,2,3,4-tetrahydrosioquinoline-3-carboxylic acid (1.1 g, yield: 89.5%). This produuct is recrystallized from methanol. m.p. 255°–256° C. (decomp.), $[\alpha]_D^{20}$ +138.1° (c=1, DMF).

Preparation 2

(a) A solution of (3S)-1-oxo-1,2,3,4-tetrahydroisoquinoline-3-carboxylic acid (1 g), silver oxide (3.64 g), methyl iodide (15 g) in DMF (25 ml) is stirred in the dark for 7 days. Insoluble materials are filtered off, and ethyl acetate (300 ml) is added to the filtrate. The mixture is washed with an aqueous 30% sodium thiosulfate solution, dried and then distilled to remove the solvent, whereby (3S)-3-methoxycarbonyl-2-methyl-1-oxo-1,2,3,4-tetrahydroisoquinoline (1.1 g) is obtained as an oil.

NMR (CDCl$_3$,δ): 2.95 (d, 2H, C$_4$—H$_2$), 3.2 (s, 3H, —OCH$_3$), 3.65 (s, 3H, —N—CH$_3$), 4.25-4.40 (dd, 1H, C$_3$—H).

(b) (3S)-3-Methoxycabonyl-2-methyl-1-oxo-1,2,3,4-tetrahydroisoquinoline (1.1 g) is dissolved in methanol (10 ml), and an aqueous 1N-sodium hydroxide solution (6 ml) is added thereto. The solution is stirred at 0° C. for one hour. The mixture is acidified with 10% HCl, and extracted with ethyl acetate. The extract is distilled to remove ethyl acetate, whereby (3S)-2-methyl-1-oxo-1,2,3,4-tetrahydroisoquinoline-3-carboxylic acid (350 mg) is obtained as crystals.

m.p. 173°–175° C.

$[\alpha]_D^{25}$ −3.3° (c=1, methanol).

IR $\nu_{max}^{nujol}$ (cm$^{-1}$): 1730.

Preparation 3

(3S)-1-Oxo-7-nitro-1,2,3,4-tetrahydroisoquinoline-3-carboxylic acid (1 g) is suspended in acetic acid (50 g), and PtO$_2$ (50 mg) is added thereto. The mixture is subjected to catalytic reduction. The catalyst is filtered off, and the filtrate is distilled to remove the solvent, whereby (3S)-1-oxo-7-amino-1,2,3,4-tetrahydroisoquinoline-3-carboxylic acid (870 mg) is obtained as an oil.

Preparation 4

(3S)-1-Oxo-7-amino-1,2,3,4-tetrahydroisoquinoline-3-carboxylic acid (850 mg) is dissolved in a mixture of dioxane (8.5 ml), water (4.2 ml) and N-sodium hydroxide (4.2 ml). Di-tert.-butyl dicarbonate (1.1 g) is added dropwise to the solution at 10°–15° C., and the mixture is stirred at room temperature overnight. The mixture is distilled under reduced pressure to remove dioxane, and the residue is washed with ethyl acetate, adjusted to pH 2 with N—H$_2$SO$_4$ and extracted with ethyl acetate. The extract is washed with water, dried and then distilled under reduced pressure to remove the solvent. Ethyl acetate is added to the residue and the crystals are colltected by filtration, whereby (3S)-1-oxo-7-tert.-butyloxycarbonylamino-1,2,3,4-tetrahydroisoquinoline-3-carboxylic acid (730 mg) is obtained as crystals.

m.p. 195°–195° C. (decomp.).

$[\alpha]_D^{25}$ +6.1° (c=1, methanol).

Preparation 5

(3RS)-3,4-dihydroisocoumarin-3-carboxylic acid (4.8 g) and D-phenylalanine amide (4.1 g) are dissolved in isopropyl alcohol (400 ml) at 80° C. The mixture is cooled gradually. The precipitated crystals are collected by filtration and recrystallized from isopropyl alcohol (the filtrates are referred to as Mother liquids I and II), whereby (3S)-3,4-dihydroisocoumarin-3-carboxylic acid.D-phenylalanine amide salt (1.8 g) is obtained.

$[\alpha]_D^{25}$ −2.2° (c=1, methanol).

The salt obtained above is dissolved in water, and the solution is acidified with 10% HCl and extracted with ethyl acetate. The extrct is dried and then distilled to remove the solvent. The residue is recrystallized from a mixture of ethyl acetate and petroleum ether, whereby (3S)-3,4-dihydroisocoumarin-3-carboxylic acid (800 mg) is obtained.

m.p. 174°–177° C.

$[\alpha]_D^{27}$ +52.2° (c=1, methanol).

IR $\nu_{max}^{nujol}$ (cm$^{-1}$): 1755, 1605.

NMR (DMSO-d$_6$δ): 3.1–3.8 (2H, C$_4$—H$_2$), 5,35 (t, 1H, C$_3$—H), 7.3–7.8 (m, 3H, C$_5$, C$_6$, C$_7$—H), 7.9–8.1 (m, 1H, C$_8$—H).

Mother liquids I and II are combined and distilled to remove the solvent. The residue is dissolved in water, and the solution is acidified with 10% HCl and extracted with ethyl acetate. The extract is distilled to remove ethyl acetate. The crystals are collected by filtration and dissolved in a mixture of isopropyl alcohol (350 ml) and L-phenylalanine amide (2.92 g) at 80° C. The mixture is cooled gradually, and the precipitated crystals are collected by filtration, whereby (3R)-3,4-dihydroisocoumarin-3-carboxylic acid.L-phenylalanine amide salt (2.82 g) is obtained.

$[\alpha]_D^{26}$ +1.0° (c=1, methanol).

The salt obtained above is treated in the same manner as mentioned above, whereby (3R)-3,4-dihydroisocoumarin-3-carboxylic acid (1.43 g) is obtained.

m.p. 173°–177° C.

$[\alpha]_D^{27}$ −51.0° (c=1, methanol). IR and NMR of the product coincide with those of (3RS) or (3S)-isomer.

Preparation 6

(a) (3S)-6,7-Dihydroxy-1,2,3,4-tetrahydroisoquinoline-3-carboxylic acid [J. Org. Chem., 26, 3533 (1961)] (33.9 g) and sodium borate.10H$_2$O (62 g) are suspended in water (500 ml). Benzoyl chloride (27.5 g) and a solution of sodium hydroxide (13 g) in water (100 ml) are added dropwise to the suspension at 0° C. under stirring. The mixture is stirred at room temperature for 4 hours. The mixture is washed with ethyl acetate, and acidified with conc. HCl, and extracted with ethyl acetate. The extract is dried and distilled to remove the solvent. The crystals are collected by filtration, washed with benzene and then recrystallized from water, whereby (3S)-2-benzoyl-6,7-dihydroxy-1,2,3,4-tetrahydroisoquinoline-3-carboxylic acid (41.7 g) is obtained.

m.p. 189°–192° C.

$[\alpha]_D^{27}$ −12.0° (c=1, methanol).

IR $\nu_{max}^{nujol}$ (cm$^{-1}$): 1760, 1590.

(b) (3S)-2-benzoyl-6,7-dihydroxy-1,2,3,4-tetrahydroisoquinoline-3-carboxylic acid (41.5 g) and potassium hydroxide (90 g) are dissolved in water (100 ml). Dimethyl sulfate (134 g) and a solution of potassium hydroxide (60.8 g) in water (100 ml) are added dropwise to the solution. The mixture is stirred at room temperature for 2 hours. The mixture is washed with ethyl acetate, acidified with conc. HCl and extracted with ethyl acetate. The extract is dried and then distilled to remove the solvent, whereby (3S)-2-benzoyl-6,7-dimethoxy-1,2,3,4-tetrahydroisoquinoline-3-carboxylic acid (32.5 g) is obtained as an oil.

IR $\nu_{max}^{nujol}$ (cm$^{-1}$): 1720, 1630.

NMR(CDCl$_3$, δ): 2.9–3.4 (m, 2H), 3.7–4.0 (m,6H, OCH$_3$×2), 4.2–5.7 (m, 3H), 6.3–6.8 (m, 2H), 7.3–7.6 (m, 5H, C$_6$H$_5$), 8.92 (s, 1H, COOH).

(c) (3S)-2-Benzoyl-6,7-dimethoxy-1,2,3,4-tetrahydroisoquinoline-3-carboxylic acid (32.5 g) and potassium carbonate (14.5 g) are dissolved in water (400 ml), and potassium permanganate (30.1 g) is added thereto gradually at 20° C. The mixture is stirred at room temperature overnight. Sodium bisulfite (10 g) is added to the mixture, and the mixture is stirred at room temperature for 2 hours. Precipitated manganese dioxide is filtered off, and the filtrate is acidified with conc.HCl. The precipitates are collected by filtration and recrystallized from a mixture of acetone and water (400 ml–500 ml), whereby N-benzoyl-(6-carboxy-2,3-dimethoxy)phenylalanine (17.7 g) is obtained.

m.p. 241°–243° C.

$[\alpha]_D^{26}$ −98.9° (c=1, N—NaOH).

IR $\nu_{max}^{nujol}$ (cm$^{-1}$): 1755, 1685, 1635.

(d) A mixture of N-benzoyl-(6-carboxy-2,3-dimethoxy)-phenylalanine (14.5 g), 6N-HCl (900 ml) and acetic acid (70 ml) is refluxed at 130° C. overnight. The mixture is distilled under reduced pressure to remove the solvent (about 800 ml of the solvent are removed). The residue is washed with benzene and then evaporated to dryness. The residue is purified with silica gel column chromotography (Solvent; chloroform:methanol:acetic acid=85:15:3). The crude product thus obtained is recrystallized from a mixture of chloroform and ethyl acetate, whereby (3S)-1-oxo-6,7-dimethoxy-1,2,3,4-tetrahydroisoquinoline-3-carboxylic acid (1.2 g) is obtained.

m.p. 212°–214° C.

$[\alpha]_D^{25}$ +32.7° (c=1, methanol).

IR $\nu_{max}^{nujol}$ (cm$^{-1}$): 1720, 1600.

Preparation 7

(a) N-Benzoyl-(6-carboxy-2,3-dimethoxy)phenylalanine (62 g) obtained in Preparation 6-(c), is suspended in a mixture of acetic acid (800 ml) and 47% hydrobromic acid (60 ml). The suspenson is refluxed at 130° C. overnight under stirring. The mixture is distilled under reduced pressure to remove acetic acid. Water is added to the residue and the solution is washed with benzene. The aqueous solution is evaporated to dryness, and methanol is added to the residue. The methanol solution is again evaporated to dryness. The residue is chromatographed on silica gel (Solvent; chloroform:acetic acid:methanol=85:6:15). Thereby the following two compounds are obtained.

Methyl (3S)-1-oxo-6,7-dihydroxy-1,2,3,4-tetrahydroisoquinoline-3-carboxylate:

Yield: 12 g.

m.p. 245°–248° C. (recrystallized from methanol).

$[\alpha]_D^{23}$ +19.8° (c=1, methanol). IR $\nu_{max}^{nujol}$ (cm$^{-1}$): 3300, 1740, 1650.

Methyl (3S)-1-oxo-6-methoxy-7-hydroxy-1,2,3,4-tetrahydroisoquinoline-3-carboxylate:

Yield: 4.36 g.

m.p. 214°–216° C. (recrystallized from methanol).

$[\alpha]_D^{23}$ +39.8° (c=1, methanol).

IR $\nu_{max}^{nujol}$ (cm$^{-1}$): 3375, 1745, 1650.

(b) Methyl (3S)-1-oxo-6,7-dihydroxy-1,2,3,4-tetrahydroisoquinoline-3-carboxylate (4 g) is dissolved in methanol (100 ml), and a solution of sodium hydroxide (0.81 g) and sodium borate (7.08 g) in water (100 ml) is added thereto. The mixture is stirred at room temperature overnight. The mixture is distilled under reduced pressure to remove methanol. The residue is acidified with conc.HCl, and the solution is chromatographed on a column (2.6×35 cm) of CHP-20P resin. The column is washed with water (500 ml), and then the product is eluted with 50% methanol. The eluate is distilled under reduced pressure to remove the solvent, and water is added to the residue. The precipitated crystals are collected by filtration and recrystallized from water, whereby (3S)-1-oxo-6,7-dihydroxy-1,2,3,4-tetrahydroisoquinoline-3-carboxylic acid (1.81 g) is obtained.

m.p. 268°–272° C.

$[\alpha]_D^{21}$ +0.7° (c=1, dimethylformamide).

IR $\nu_{max}^{nujol}$ (cm$^{-1}$): 3300, 1730.

In the same manner as described above, (3S)-1-oxo-6-methoxy-7-hydroxy-1,2,3,4-tetrahydroisoquinoline-3-carboxylic acid is obtained from 4.0 g of methyl (3S)-1-oxo-6-methoxy-7-hydroxy-1,2,3,4-tetrahydroisoquinoline-3-carboxylate.

Yield: 3.08 g.

m.p. 280°–285° C. (recrystallized from water).

$[\alpha]_D^{21}$ +42.3° (c=1, dimethylformamide).

IR $\nu_{max}^{nujol}$ (cm$^{-1}$): 3400, 1715, 1610.

What we claim is:

1. A compound of the formula:

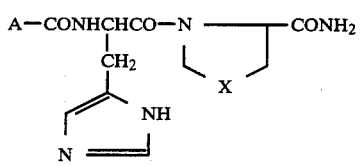  (I)

wherein A is a group of the formula:

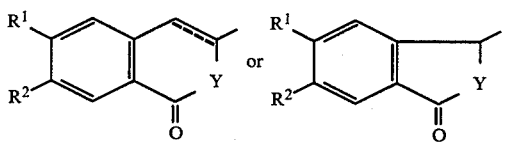

$R^1$ and $R^2$ are the same or different and each hydrogen atom, nitro, amino, a protected amino, hydroxy or lower alkoxy, Y is oxygen atom or a group of the formula: —NR$^3$—, $R^3$ is hydrogen atom or lower alkyl, X is methylene or sulfur atom and the dotted line is an optional double bond, or a pharmaceutically acceptable acid addition salt thereof.

2. The compound of claim 1, wherein $R^1$ and $R^2$ are the same or different and each hydrogen atom, nitro, amino, lower alkoxycarbonylamino, hydroxy or methoxy and $R^3$ is hydrogen atom or methyl.

3. The compound of claim 2, wherein A is a group of the formula:

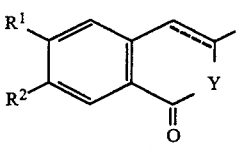

$R^1$ and $R^2$ are the same or different and each hydrogen atom, nitro, amino, tert-butoxycarbonylamino, hydroxy or methoxy, Y is oxygen atom or a group of the formula: —NR$^3$—, $R^3$ is hydrogen atom or methyl and the dotted line is an optional double bond.

4. The compound of claim 3, wherein $R^1$ and $R^2$ are the same or different and each hydrogen atom, nitro or amino, Y is a group of the formula: —NR$^3$—, $R^3$ is hydrogen atom or methyl, X is methylene and the dotted line is an optional double bond.

5. The compound of claim 4, wherein A is a group of the formula:

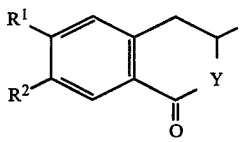

$R^1$ and $R^2$ are the same or different and each hydrogen atom or amino

Y is a group of the formula: —NR$^3$—, $R^3$ is hydrogen atom or methyl and

X is methylene.

6. The compound of claim 5, wherein A and other constituent amino acid residues are all of the S-configuration.

7. The compound of claim 6, which is N$^\alpha$-[(3S)-1-oxo-1,2,3,4-tetrahydroisoquinoline-3-carbonyl]-L-histidyl-L-prolinamide or a pharmaceutically acceptable acid addition salt thereof.

8. The compound of claim 6, which is N$^\alpha$-[(3S)-2-methyl-1-oxo-1,2,3,4-tetrahydroisoquinoline-3-carbonyl]-L-histidyl-L-prolinamide or a pharmaceutically acceptable acid addition salt thereof.

9. The compound of claim 6, which is N$^\alpha$-[(3S)-1-oxo-7-amino-1,2,3,4-tetrahydroisoquinoline-3-carbonyl]-L-histidyl-L-prolinamide or a pharmaceutically acceptable acid addition salt thereof.

* * * * *